(12) United States Patent
Katra et al.

(10) Patent No.: US 10,292,611 B2
(45) Date of Patent: May 21, 2019

(54) SYSTEM AND METHOD FOR ONSET/OFFSET CAPTURE

(71) Applicant: Medtronic Monitoring, Inc., San Jose, CA (US)

(72) Inventors: Rodolphe Katra, Blaine, MN (US); Scott Williams, Minneapolis, MN (US); Niranjan Chakravarthy, Eden Prairie, MN (US)

(73) Assignee: Medtronic Monitoring, Inc., San Jose, CA (US)

(*) Notice: Subject to any disclaimer, the term of this patent is extended or adjusted under 35 U.S.C. 154(b) by 131 days.

(21) Appl. No.: 15/340,632

(22) Filed: Nov. 1, 2016

(65) Prior Publication Data
US 2018/0116536 A1 May 3, 2018

(51) Int. Cl.
| | | |
|---|---|---|
| A61B 5/04 | (2006.01) | |
| A61B 5/00 | (2006.01) | |
| A61B 5/0452 | (2006.01) | |
| A61B 5/0432 | (2006.01) | |
| A61B 5/046 | (2006.01) | |

(52) U.S. Cl.
CPC .......... *A61B 5/04012* (2013.01); *A61B 5/046* (2013.01); *A61B 5/0452* (2013.01); *A61B 5/04325* (2013.01); *A61B 5/4848* (2013.01); *A61B 5/7285* (2013.01); *A61B 5/7289* (2013.01)

(58) Field of Classification Search
CPC ............ A61B 5/04012; A61B 5/04325; A61B 5/0452; A61B 5/046; A61B 5/4848; A61B 5/7285; A61B 5/7289

USPC ......................................................... 600/15
See application file for complete search history.

(56) References Cited

U.S. PATENT DOCUMENTS

| | | | |
|---|---|---|---|
| 6,922,584 B2 | 7/2005 | Wang et al. | |
| 7,031,765 B2 | 4/2006 | Ritcher et al. | |
| 7,280,869 B2 | 10/2007 | Warman et al. | |
| 7,447,544 B1 * | 11/2008 | Kroll ...................... | A61N 1/025 600/508 |
| 7,634,310 B2 | 12/2009 | Lee et al. | |
| 8,790,259 B2 | 7/2014 | Katra et al. | |
| 8,965,498 B2 | 2/2015 | Katra et al. | |

(Continued)

OTHER PUBLICATIONS

Notification of Transmittal of the International Search Report and the Written Opinion of the International Searching Authority, or the Declaration for PCT/US2017/059458 dated Jan. 26, 2018.

(Continued)

*Primary Examiner* — Carl H Layno
*Assistant Examiner* — Erin M Piateski
(74) *Attorney, Agent, or Firm* — Billion & Armitage; Michael A. Collins (57) ABSTRACT

A medical device is utilized to monitor physiological parameters of a patient and capture segments of the monitored physiological parameters. The medical device includes circuitry configured to monitor one or more physiological parameters associated with the patient and an analysis module that includes a buffer and a processor. The buffer stores monitored physiological parameters and the processor analyzes the monitored physiological parameters and triggers capture of segments from the buffer in response to a triggering criteria being satisfied. The analysis module selects a pre-trigger duration based at least in part on the triggering criteria.

9 Claims, 8 Drawing Sheets (56) References Cited

U.S. PATENT DOCUMENTS

| | | |
|---|---|---|
| 9,173,615 B2 | 11/2015 | Katra et al. |
| 9,314,178 B2 | 4/2016 | Katra et al. |
| 2007/0255147 A1 | 11/2007 | Drew et al. |
| 2008/0221633 A1 | 9/2008 | Linker |
| 2013/0274584 A1 | 10/2013 | Finlay et al. |
| 2014/0371604 A1 | 12/2014 | Katra et al. |
| 2015/0126822 A1 | 5/2015 | Chavan et al. |
| 2016/0135708 A1 | 5/2016 | Chakravarthy et al. |
| 2016/0220139 A1 | 8/2016 | Mahajan et al. |

OTHER PUBLICATIONS

Garcia, et al., "Arrhythmia Recognition, The Art of Interpretation", Jones & Bartlett Learning, First Edition, Nov. 12, 2003, 392-393, 534-535.

* cited by examiner

SYSTEM AND METHOD FOR ONSET/OFFSET CAPTURE

TECHNICAL FIELD

This invention relates generally to systems and methods of patient monitoring and in particular to systems and methods of detecting onset and/or offset of detected conditions.

BACKGROUND

Patient monitoring has become prevalent both inside and outside of a hospital, allowing physiological parameters of a patient to be monitored. Sensors utilized to collect these physiological parameters include electrocardiogram (ECG) circuitry, accelerometers, respiration sensors, etc. Physiological parameters monitored may include cardiac rhythm, activity level, posture, breathing rate, and others. In particular, cardiac monitoring of patients both inside and outside of a hospital has become more prevalent, with cardiac devices/monitors being utilized to detect arrhythmic conditions (e.g., any abnormality or perturbation in the normal electrical rhythm of the heart). Examples of arrhythmias include premature atrial contractions, premature ventricular contractions, atrial fibrillation, atrial flutter, ventricular tachycardia, ventricular fibrillation, bradycardia, and others. Cardiac arrhythmias may be accompanied by symptoms, or by no symptoms at all. Similarly, other types of monitoring devices may be utilized to detect other patient conditions.

Detection of abnormal conditions typically requires analysis of the monitored physiological parameter and comparison to a trigger criteria. Satisfaction of the trigger criteria typically results in at least a portion (i.e., segment) of the monitored physiological parameter being stored and/or communicated to a healthcare professional (HCP) for review. For diagnostic purposes, it may be beneficial to include in the captured segment the onset of the abnormal condition (e.g., the monitored physiological signal just prior to onset of the abnormal condition). This information may be valuable in diagnosing the cause or abnormal condition. Likewise, it may be beneficial to include in the captured segment (or subsequently captured segment) the offset of the abnormal condition (e.g., the monitored physiological signal following the offset or send of the abnormal condition). However, the capture of segments of monitored physiological parameters in response to a trigger criteria typically relies on a predetermined duration of time prior to and following the trigger event. With the various types of physiological parameters and various trigger criteria being utilized (both of which affect the duration of time required to trigger capture of an event), it is difficult to ensure that the onset/offset of the abnormal condition is captured.

BRIEF SUMMARY OF THE INVENTION

According to an embodiment, a medical device is utilized to monitor physiological parameters of a patient and capture segments of the monitored physiological parameters. The medical device includes circuitry configured to monitor one or more physiological parameters associated with the patient and an analysis module that includes a buffer and a processor. The buffer stores monitored physiological parameters and the processor analyzes the monitored physiological parameters and triggers capture of segments from the buffer in response to a triggering criteria being satisfied. The analysis module selects a pre-trigger duration based at least in part on the triggering criteria.

According to one embodiment, a method of capturing onset and/or offset of detected abnormal conditions includes selecting a pre-trigger duration based on a trigger criteria. The method further includes monitoring physiological parameters of a patient and triggering the capture of a segment of the monitored physiological parameters in response to the trigger criteria being satisfied, wherein captured segments have a duration defined at least in part by the selected pre-trigger duration.

According to another embodiment a method of monitoring and capturing arrhythmic electrocardiogram (ECG) segments includes monitoring one or more physiological parameters of a patient. The method further includes triggering capture of a first segment in response to an onset trigger criteria being satisfied and triggering capture of a second segment in response to an abnormal condition trigger criteria being satisfied. The first segment is discarded in the event that capture of the first segment is not followed by the triggering of the abnormal condition trigger, wherein the onset trigger criteria is more sensitive than the abnormal condition trigger criteria.

DETAILED DESCRIPTION

The present invention provides a system and method of monitoring physiological parameters and capturing segments of the monitored physiological parameters representing a detected abnormal condition. In particular, the present invention provides systems and methods of ensuring that captured segments include at least one of the onset and/or offset of detected abnormal condition. Monitored physiological parameters may include one or more of electrocardiogram (ECG) signals, accelerometer signals, respiration signals, bio-impedance signals, as well as others. There are several benefits of capturing onset/offset of abnormal conditions. For example, with respect to conditions such as arrhythmias, the time between onset of the arrhythmia and triggering of the arrhythmia may be indicative of the severity and/or progression of the arrhythmia. As an arrhythmia becomes more serious, the time required for the arrhythmia to organize decreases, resulting in a decrease in time between onset of the arrhythmia and triggering of the arrhythmia. Monitoring of changes in this time—made possible via ensured detection and identification of arrhythmia onset—allows a health care profession (HCP) to monitor both severity of the condition and whether the condition is worsening (is the time between onset and trigger getting shorter). In addition, if the underlying condition is being treated, measurement of onset to trigger may be utilized to determine the efficacy of treatment.

The present disclosure presents a number of systems and methods of ensuring the capture of onset and/or offset conditions. For example, one embodiment ensures capture of onset by selecting a pre-trigger duration based on the trigger criteria utilized to detect the abnormal condition (e.g., number of beats required, heart rate threshold, activity amplitude, etc.) to ensure that the captured segment includes the onset of the detected condition. In other embodiments, at least a first and second trigger criteria are utilized, wherein the first trigger criteria has a high sensitivity level that is utilized to capture a first segment corresponding with onset of the abnormal condition and a second trigger criteria has a low (or lower) sensitivity level that is utilized to trigger capture of a second segment corresponding with the trigger event. In this way, the first segment ensures the onset condition is captured, while the second segment ensures the trigger event is captured. In this embodiment, the first segment is only retained if the second trigger criteria is subsequently satisfied.

In general, the disclosure describes utilization of trigger criteria utilized to trigger the capture of abnormal conditions, and systems and methods of ensuring the capture of the onset of the abnormal condition. As discussed above, this may include properly selecting the pre-trigger duration and/or utilizing a two or more trigger criteria. However, these concepts may also be applied to the capture of the offset or end of the abnormal condition. In some embodiments, the same criteria utilized to detect the abnormal condition is applied to detect the offset or end of the abnormal condition (leading to capture of the segment that includes offset). For example, this may include properly selecting the pre-trigger offset duration and/or utilizing two or more offset trigger criteria.

A number of the examples provided describe ECG monitoring and the detection of arrhythmic conditions, but it should be understood that the present invention may be applicable in monitoring other types of physiological parameters and with respect to other types of abnormal conditions beyond arrhythmias. As discussed above, other physiological parameters monitored may include accelerometer signals used to determine posture and/or activity of the patients, as well as bio-impedance signals, respirations signals, and others. With respect to each, ensuring the capture of the portion of the signal representing onset of the abnormal condition and/or offset of the abnormal condition is beneficial.

Figure 1:
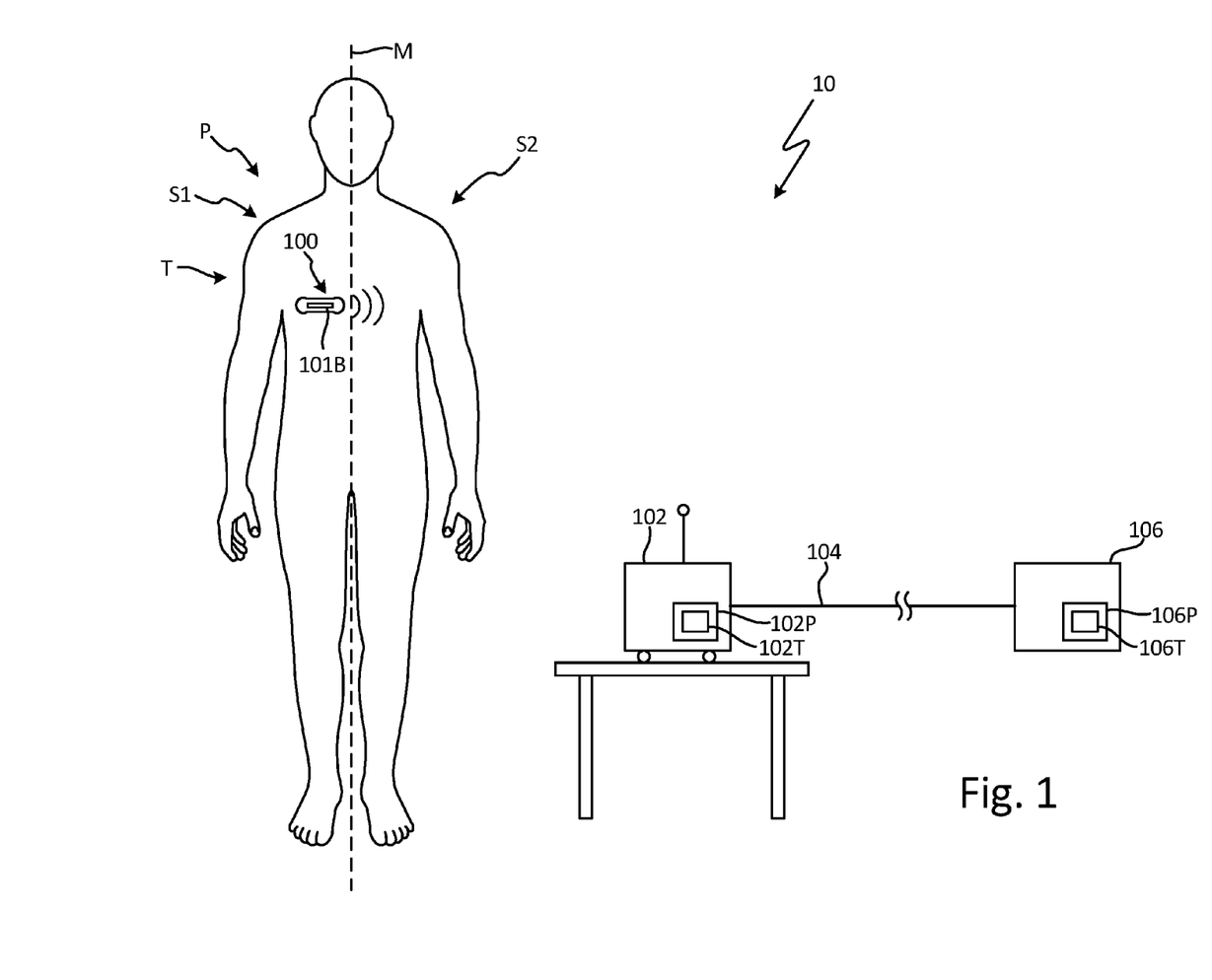
FIG. 1 is a schematic diagram of a monitoring system according to an embodiment of the present invention.

FIG. 1 illustrates a patient P and a monitoring system 10, according to one or more embodiments of the present disclosure for monitoring physiological parameters of the patient. Patient P comprises a midline M, a first side S1, for example a right side, and a second side S2, for example a left side. Monitoring system 10 comprises a patient medical device 100, gateway 102, and remote monitoring center 106.

In the embodiment shown in FIG. 1, patient medical device 100 is an adherent device that attaches to the skin of the patient, but in other embodiments may be an implantable device, an insertable device, an injectable device, or a wearable device such as a Holter monitor (collectively referred to as a medical device). Each of these devices has advantages and disadvantages, in terms of battery life, memory, communication capabilities, etc. It is assumed that some combination of battery life, memory costs, communication capabilities, etc. places a limit on the amount of data captured in response to a trigger event (e.g., detection of an abnormal condition) such as an arrhythmia. As discussed in more detail with respect to FIG. 2, capturing an ECG segment means the segment is stored more permanently by medical device 100, or even communicated to remote center 106.

As discussed above, it would be beneficial to store segments that include the onset of the abnormal condition (i.e., the ECG signal just prior to onset of the arrhythmic condition), as well as the offset of the abnormal condition (i.e., the ECG signal just after the end of the arrhythmia), as well as the trigger event associated with the abnormal condition. However, whether the onset and offset of the abnormal condition is captured depends on the size of the stored segment (specifically, the pre-trigger and post-trigger durations of the triggering segment). However, increasing the size of each segment increases the costs associated with capturing, storing, and communicating the segment. Embodiments of the present invention balance the costs of employing large segments while ensuring that onset and/or offsets of the abnormal conditions are captured.

Embodiments of suitable medical devices are described in more detail with respect to FIGS. 6 and 7, below. In general, medical device 100 is described herein as providing a monitoring function, but in other embodiments may be configured to provide treatment as well.

Medical device 100 can be adhered/injected/inserted to a patient P at many locations, for example thorax T of patient P. In many embodiments, the device may adhere to one side of the patient, from which side data can be collected. A benefit of utilizing an adherent device, implantable, or injectable device is that it may be utilized to collect physiological data from the patient while the patient goes about normal day-to-day activities outside of a hospital setting. Medical device 100 may monitor a number of physiological parameters associated with patient P, including electrocardiogram (ECG) signals utilized to detect rhythm abnormalities such as tachycardia, bradycardia, atrial fibrillation, etc. as well as accelerometer data utilized to detect activity level data, posture, and bio-impedance data utilized to detect hydration, respiration, etc. Analysis of the ECG signals to detect rhythm abnormalities may be done locally by medical device 100 or remotely by gateway 102 and/or remote monitoring center 106 (or similar platform separate from medical device 100).

In embodiments in which the physiological data is analyzed locally by medical device 100, trigger criteria are utilized to detect abnormal conditions and initiate the capture of segments representative of the detected abnormal condition. The captured segment may be subsequently transmitted to remote monitoring center 106 for review by a human expert/physician (i.e., a health care professional (HCP)). Communication of the captured segment may be immediate, or may be delayed for a period of time (i.e., until it is possible/cost effective to communicate the stored segment). In response to the received segment, the HCP may verify the detected abnormality and take appropriate steps (e.g., prescribe treatment).

In other embodiments in which monitored physiological signals are not analyzed by medical device 100 locally, monitored signals are communicated to an external processor such as gateway 102 or remote monitoring center 106 for analysis and detection of abnormalities. As discussed above, gateway 102 and/or remote monitoring center 106 would similarly utilize trigger criteria to detect abnormal conditions and initiate the capture of segments representative of the detected abnormality. In response to a detected abnormality, a segment corresponding with the detected abnormality is captured and stored for subsequent review by a HCP.

In the embodiment shown in FIG. 1, medical device 100 communicates wirelessly with remote center 106. The communication may occur directly (via a cellular or Wi-Fi network), or indirectly through intermediate device or gateway 102. As described above, in one embodiment physiological signals monitored by medical device 100 are communicated in their entirety to remote center 106 for analysis. In other embodiments, medical device 100 processes the monitored signals locally using trigger criteria to detect abnormalities and stores/captures segments corresponding with detected abnormalities.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by HCPs to verify accuracy. Reports may then be generated at remote monitoring center 106 for communication to the HCPs, including physicians and nurses. In one embodiment, in addition to one-way communication from medical device 100 to gateway 102 and/or remote monitoring center 106, remote monitoring center 106 may communicate/push settings to medical device 100, either to program/initialize medical device 100 or update the values stored by medical device 100. As discussed in more detail below, this may include selecting the trigger criteria to utilize, and/or selecting the size of the segments (e.g., pre-trigger duration and/or post-trigger duration).

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG samples—monitored by medical device 100 may be analyzed by one or more of the distributed processors included as part of medical device 100, gateway 102, and/or remote monitoring center 106.

Figure 2:
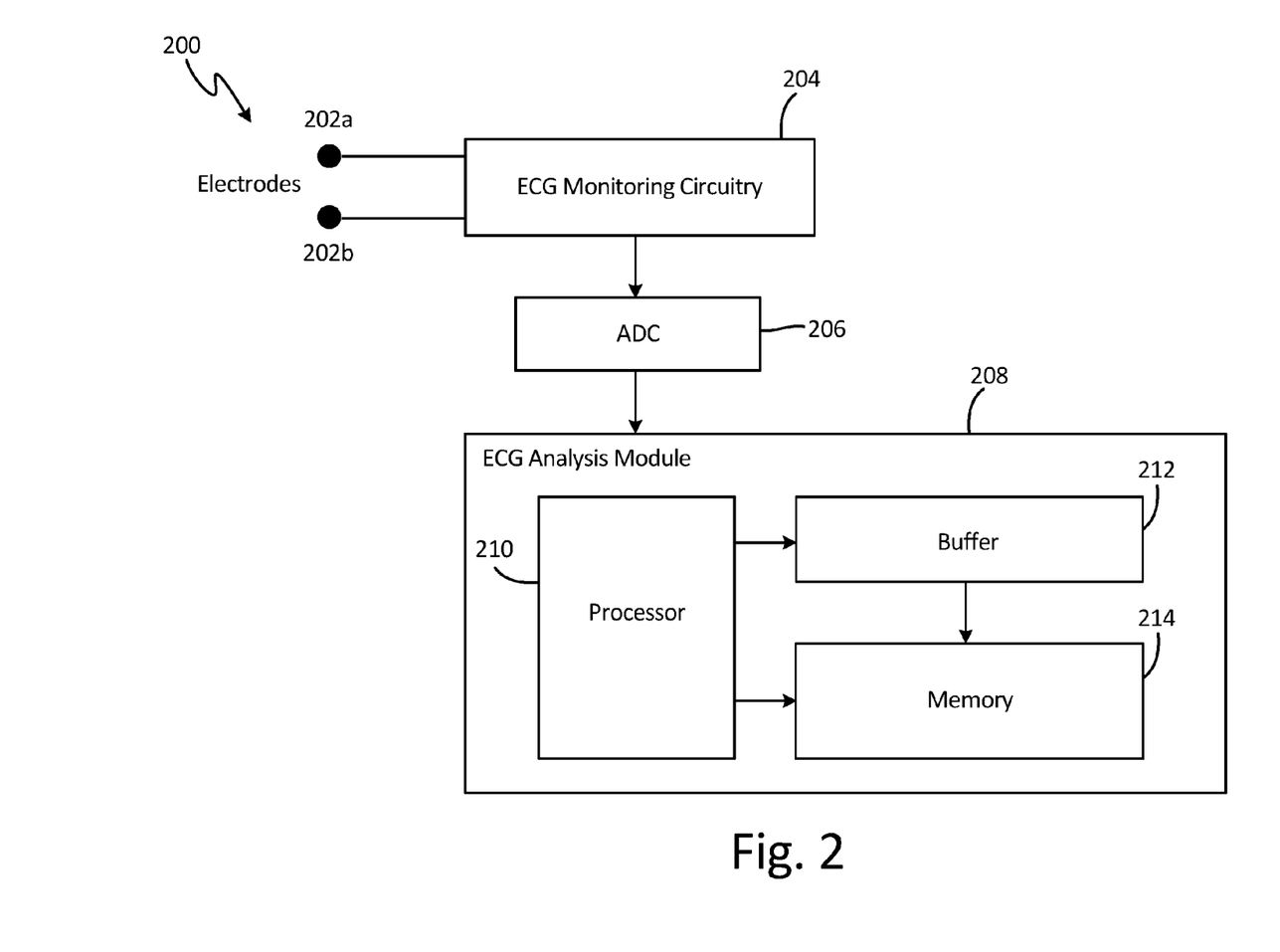
FIG. 2 is a block diagram of a medical device configured to monitor one or more physiological parameters according to an embodiment of the present invention.

FIG. 2 is a block diagram of components utilized by medical device 200 to monitor physiological parameters and capture segments according to an embodiment of the present invention. The embodiment shown in FIG. 2 is directed specifically to monitoring ECG signals associated with the patient, and detecting rhythm abnormalities (e.g., arrhythmias) that result in ECG segments being captured. In other embodiments, however, other types of physiological parameters may similarly be analyzed to detect abnormalities. Medical device 200 includes electrodes 202a, 202b, ECG monitoring circuitry 204, analog-to-digital converter 206, and ECG analysis module 208, which includes processor 210, buffer 212 and memory 214.

In the embodiment shown in FIG. 2, a pair of electrodes 202a and 202b are positioned on the patient to monitor electrocardiogram (ECG) signals. In other embodiments, a single electrode may be utilized in conjunction with a ground terminal or conversely a plurality of electrodes may be utilized to monitor patient ECG signal. In addition, electrodes 202a and 202b may be implanted, subcutaneous, or adherent. For example, electrodes 202a and 202b may be included on intracardiac leads utilized by an implantable device. In other embodiment, electrodes 202a and 202b may be included as part of an insertable device in which the electrodes are located subcutaneously. In still other embodiments electrodes 202a and 202b may be included as part of an adherent device in which electrodes are affixed to the skin of the patient.

ECG monitoring circuitry 204 is configured to monitor ECG signals sensed by electrodes 202a and 202b. ECG monitoring circuitry 204 may include filtering and pre-processing of the ECG signal prior to conversion of the analog signal to a digital signal by analog-to-digital converter (ADC) 206. ECG analysis module 208 receives the filtered, digital ECG signal and processes the ECG signal to detect arrhythmic conditions. In the embodiment shown in FIG. 2, ECG analysis module 208 includes processor 210, buffer 212 and memory unit 214. In this embodiment, ECG analysis module 208 receives ECG signals from EGG monitoring circuit 204 and ADC 6 and stores the monitored ECG signals temporarily into buffer 212. While ECG signals are stored to buffer 212, processor 210 analyzes the ECG signal using one or more trigger criteria. In response to a triggering event (i.e., trigger criteria met), the ECG segment stored to buffer 212 is saved to memory 214. A variety of trigger criteria may be utilized to detect rhythm abnormalities. In one embodiment, morphology of monitored ECG beats are utilized to detect abnormalities (e.g., premature ventricular contractions (PVCs)). In other embodiments, rate-based arrhythmias (e.g., tachycardia, bradycardia, etc.) are detected using a trigger criteria that requires a number of beats (X) be observed to exceed a threshold level (or fall below a threshold level in the term of bradycardia monitoring) out of a total number of beats (Y) in order to trigger capture of the arrhythmic; ECG segment. The number of beats (X) required may be required to be consecutive beats or may be non-consecutive. In this example, exceeding the trigger criteria means an arrhythmia has been detected. Similarly, a trigger offset criteria defines the beat criteria that results in a determination that the arrhythmia has ended (e.g. number of beats below a threshold out of a total number of betas). In some embodiments, the trigger offset criteria is the same as the trigger onset criteria. For example, an arrhythmia detected when the trigger criteria is exceeded may trigger offset detection when the observed beats fall below the trigger criteria. In other embodiments, the trigger offset criteria may be different than the trigger criteria.

In one embodiment, the ECG signal is stored to buffer 212 on a rolling basis. That is, old ECG data is re-written with new ECG data. For example, buffer 212 may be implemented with a circular buffer that results in the oldest data being rewritten. The size of buffer 212 is typically substantially smaller than the size of memory 214, wherein ECG segments captured from buffer 212 are stored to memory 214. Stored ECG segments may then be communicated to remote monitoring center 106 for review or download at a later time. The size of buffer 212 may determine the duration or length of each stored ECG segments. In some embodiments, the size of buffer 210 is fixed, while in other embodiments the size of buffer 210 may be determined based on the trigger criteria utilized to trigger capture of arrhythmic events. In other embodiments, rather than a circular buffer, buffer 212 stores ECG segments of a determined size/length to be analyzed, but does not do so on a rolling basis. That is, if the buffer is capable of storing two minutes of ECG signals, then a first ECG segment is stored to the buffer and analyzed for arrhythmic conditions. If no arrhythmia is detected then the first ECG segment is discarded and the buffer is populated with a second ECG segment. However, as discussed in more detail with respect to FIG. 6, below, this presents the possibility that onset of an arrhythmia will occur during the first ECG segment, but will not trigger detection until the second ECG segment, at which point the first ECG segment has been discarded and onset of the arrhythmia lost. Embodiments of the present invention address capture of onset and/or offset for each of the various types of buffers that may be utilized.

As discussed above, it is beneficial to include arrhythmia onset and/or the arrhythmia offset segment (i.e., the ECG segment preceding onset of the arrhythmia and the ECG segment following offset of the arrhythmia) in the captured ECG segment(s). However, capture of ECG onset/offset depends in part on the size of buffer 212, the trigger criteria utilized, and the heart rate of the patient during the arrhythmia. In one embodiment, the trigger criteria may require 20 beats to exceed or be greater than the respective rate threshold (e.g., 130, 150, 165, 180 BPM), or meet some other criteria such as beat morphology criteria utilized to detect AF arrhythmias. The trigger criteria can be converted to an expected length of time required to monitor the ECG signal. For example, 20 beats at the heart rates of [130, 150, 165, and 180] will occur in [9.2, 8, 7.3, and 6.7 seconds], respectively. So long as the ECG segment pre-trigger duration (i.e., the length of the ECG segment captured prior to trigger) is longer than approximately 9.2 seconds, the onset of the arrhythmia will be captured. However, in embodiments in which the trigger criteria is modified (e.g., requiring either more beats to exceed the threshold, utilizing more total beats, or allowing non-consecutive beats), then the time from onset to the trigger criteria being satisfied is increased and the ECG pre-trigger duration will be insufficient to capture onset unless adjusted. The same applies to utilization of an offset trigger criteria, in which a number of beats (X) out of a total number of beats (Y) must satisfy a rate threshold or other criteria to trigger offset of the arrhythmia. Proper selection of the offset pre-trigger duration ensures capture of offset of the arrhythmia. In one embodiment, selection of pre-trigger durations takes into account the trigger criteria, including number of beats required to satisfy the trigger criteria, whether the beats are consecutive or non-consecutive beats, and the expected heart rate both of the trigger criteria beats and non-trigger criteria beats.

Figure 3:
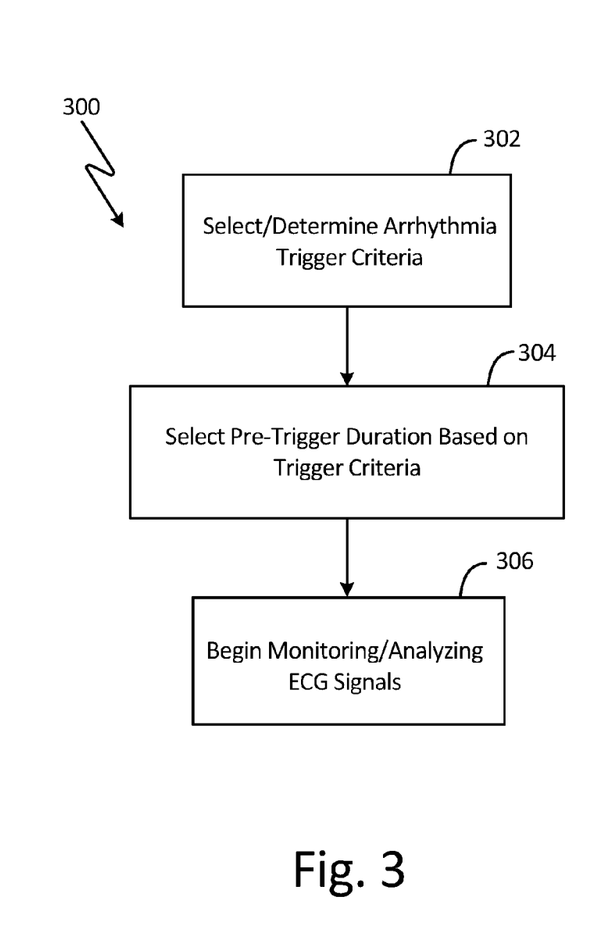
FIG. 3 is a flowchart that illustrates selecting ECG episode pre and post trigger durations according to an embodiment of the present invention.
Figure 4:
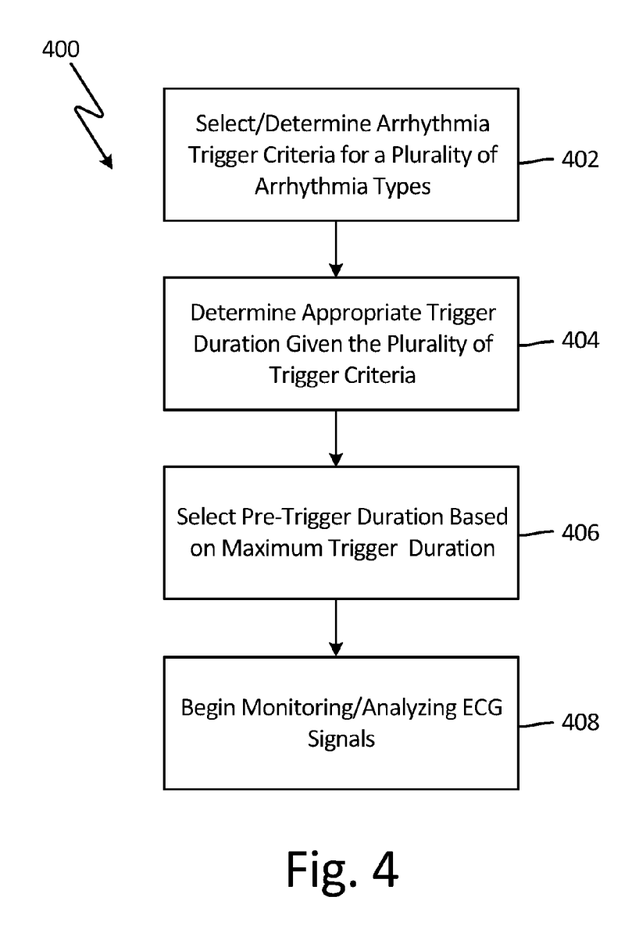
FIG. 4 is a flowchart that illustrates selecting ECG episode pre and post trigger durations based on a plurality of arrhythmia trigger criteria and arrhythmia types according to an embodiment of the present invention.
Figure 5:
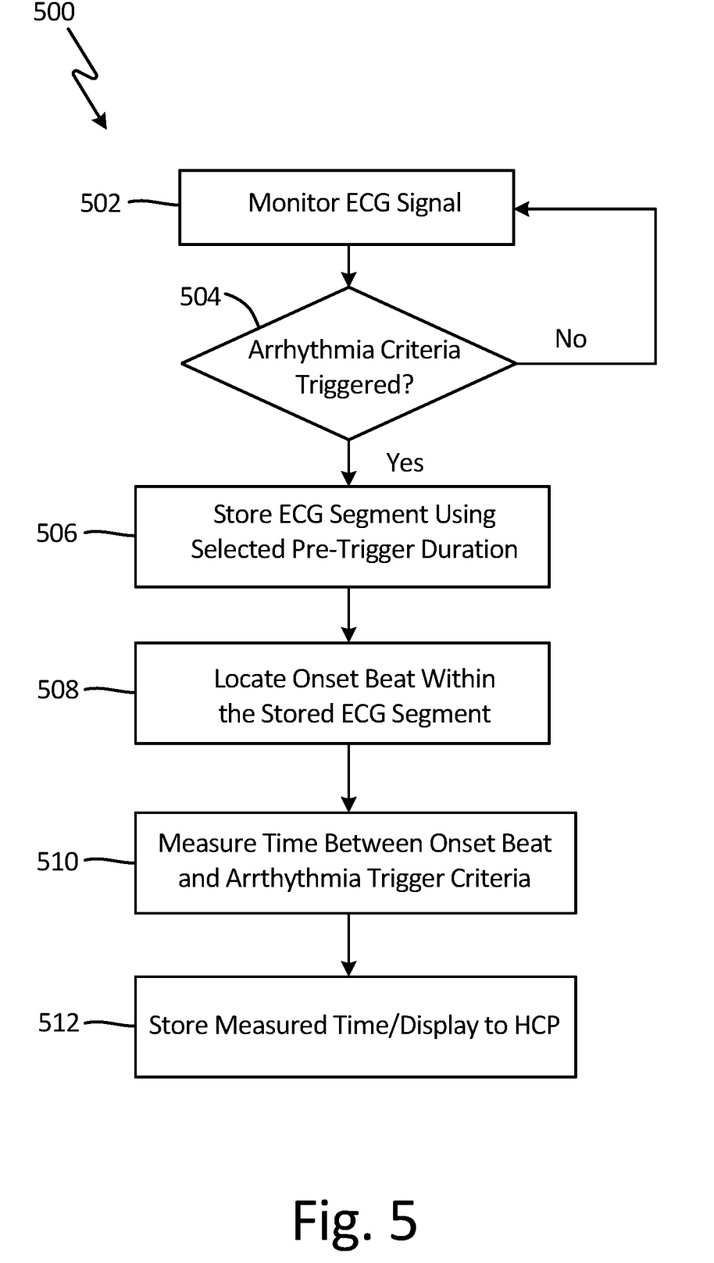
FIG. 5 is a flowchart that illustrates monitoring of ECG signals utilizing pre-trigger durations according to an embodiment of the present invention.
Figure 6:
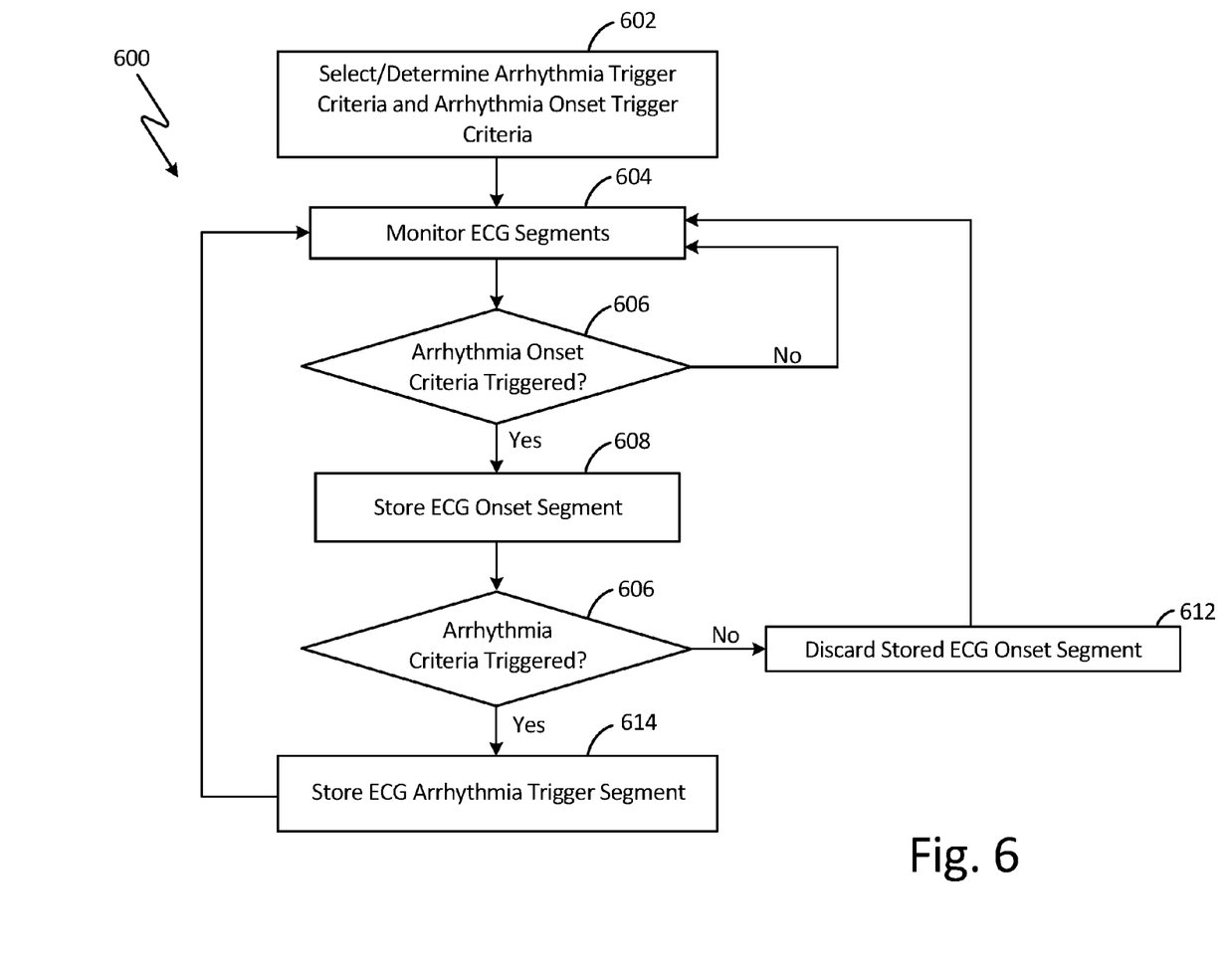
FIG. 6 is a flowchart that illustrates utilization of an arrhythmia trigger criteria and a onset trigger criteria according to an embodiment of the present invention

As discussed in more detail with respect to FIGS. 3-6, a plurality of methods may be utilized to ensure capture of the onset, trigger and/or offset of the arrhythmia. In one embodiment, onset, trigger and/or offset of the arrhythmia are captured via proper selection of the arrhythmia pre-trigger duration and offset pre-trigger duration. The arrhythmia pre-trigger duration represents the length and/or duration of ECG signal capture prior to a triggering event, and the offset pre-trigger duration represents the length and/or duration of the ECG signal captured prior to an offset triggering event. For example, FIG. 3 describes an embodiment in which the ECG episode pre-trigger duration is selected in response to the trigger criteria (e.g., number of beats required, consecutive or non-consecutive, etc.) being utilized and the types of arrhythmias being detected. The type of arrhythmia being detected may be utilized to estimate the expected heart rate during trigger such that a proper pre-trigger duration can be selected. For example, a ventricular tachycardia that requires 20 beats above a threshold heart rate of 150 BPM can utilize the expected heart rate (e.g., greater than 150 BPM) in calculating the pre-trigger duration required. The same is true for other types of arrhythmias being detected, including AF, bradycardia, and others. FIG. 4 describes an embodiment in which a plurality of different trigger criteria are provided with respect to a plurality of different arrhythmia types, wherein the ECG episode pre-trigger duration is selected based on the appropriate pre-trigger duration required for the plurality of trigger criteria and/or arrhythmia types. FIG. 6 describes an embodiment in which ECG onset is captured via utilization of an arrhythmia trigger and a separate onset trigger, in which the onset trigger utilizes a higher sensitivity to capture arrhythmia onsets prior to triggering of the trigger criteria.

FIG. 3 is a flowchart 300 that illustrates selecting ECG episode pre- and post-trigger durations according to an embodiment of the present invention. In the embodiment shown in FIG. 3, pre-trigger durations are determined for at least one type of arrhythmia using at least one arrhythmia trigger criteria. In other embodiments, medical device 200 (shown in FIG. 2) may utilize a plurality of arrhythmia trigger criteria to detect a plurality of different arrhythmia types. For each arrhythmia trigger criteria and/or offset trigger criteria, a unique pre-trigger duration and/or offset pre-trigger duration may be determined to ensure capture of ECG onset and/or offset. Post-trigger durations may also be selected.

At step 302, an arrhythmia trigger criteria is selected and/or determined. In one embodiment, the arrhythmic trigger criteria is predetermined (i.e., programmed). In other embodiments, the arrhythmic trigger criteria may be determined or modified by a health care professional (HCP) or automatically adjusted by the monitoring algorithm. The arrhythmic trigger criteria may be rhythm based, or may be triggered by the triggering criteria of another sensor being satisfied, such as a respiratory trigger, activity trigger, abrupt change trigger, or other combinations of triggers associated with monitored physiological parameters. As discussed above, in one embodiment an arrhythmic trigger criteria is represented as a ratio of beats (X) that must exceed a threshold criteria (rate-based or otherwise) out of a total number of beats (Y). The number of beats required to exceed the criteria may be defined as consecutive beats or non-consecutive beats. For example, in the case of a tachycardia, the trigger criteria may be defined to require that 13 beats out of a total of 20 beats must exceed a heart rate threshold of 150 BPM. Similarly, in the case of a bradycardia, the trigger criteria may be defined to require that 4 beats out of a total of 5 beats must be less than a heart rate threshold of 40 BPM. The selection/determination of trigger criteria at step 302 may also include selection/determination of offset trigger criteria utilized to detect the end of a detected arrhythmia. The offset trigger criteria may be the same as or different than the trigger criteria utilized to detect the arrhythmia.

At step 304, ECG episode pre-trigger durations are selected based on the selected/determined arrhythmia trigger criteria. In particular, the ECG episode pre-trigger duration is selected to ensure that onset of the arrhythmia is included in the captured ECG segment. For example, in one embodiment if X number of consecutive beats above a threshold value are required to satisfy the trigger criteria, the maximum time required for this condition to be met can be calculated and the ECG episode pre-trigger duration can be selected to be greater than the maximum time. In another example, if X number of non-consecutive beats above a threshold are required within Y total beats, then determination of the pre-trigger duration may take into account the interspersion of low-rate beats (with respect to tachycardia detection). Thus, assumptions may be made about the expected rate of interspersed low-rate beats and the pre-trigger duration may be determined to accommodate the interspersion of low-rate beats with arrhythmic beats. For example, if 13 beats out of 20 total beats are required to exceed 130 BPM, worst-case scenarios may be calculated in which 7 beats less than 40 BPM are interspersed between the 13 beats over 130 BPM. This worst-case scenario (from the perspective of capturing arrhythmia onset with the pre-trigger duration) may be utilized to select a pre-trigger duration. In other embodiments, the worst-case scenario may be based on the denominator utilized in the X number of beats out of a total of Y beats (X/Y). In the above example, the 20 total beats is utilized to determine the pre-trigger duration. In other embodiments, rather than just select the pre-trigger duration to capture the onset (or offset) of the arrhythmia (or abnormal condition), an additional buffer of time may be added to the pre-trigger duration to ensure capture of the onset as well as a buffer of time to provide additional context to the HCP regarding events that led up to the detected abnormality. In one embodiment the buffer of time added to the pre-trigger duration is fixed, while in other embodiments the buffer of time is proportional to the pre-trigger duration (e.g., 20% of the pre-trigger duration).

In addition, ECG segments are captured in response to the algorithm detecting de-assertion of an arrhythmia (i.e., ending of an arrhythmic episode). The de-assertion or offset trigger may be the same as the arrhythmic trigger criteria (i.e., if X beats out of Y total beats are required to exceed a threshold to initiate capture of an arrhythmia, then when X beats out of Y total beats do not exceed the threshold, de-assertion of the arrhythmia is triggered). In other embodiments, de-assertion of the arrhythmia is initiated in response to a change in morphology of the monitored ECG or a change in the dominant frequency of the monitored ECG. As discussed above, the offset trigger criteria and trigger criteria may be the same or different. Likewise, the offset pre-trigger duration may be the same or different than the ECG pre-trigger duration. Unlike the pre-trigger duration, the offset pre-trigger duration may be modified to account for all beats being less than a threshold. For example, to ensure capture of the arrhythmia offset condition, the offset pre-trigger duration for a tachycardia event may account for the time required to determine de-assertion of the arrhythmia if all the beats are relatively slow beats (e.g., all less than 60 BPM). In this way, the ECG pre-trigger duration is determined to ensure capture of the onset of the arrhythmia, while the offset pre-trigger duration is determined to ensure capture of the offset of the arrhythmia.

At step 306, ECG signals are monitored and analyzed using the selected/determined arrhythmia trigger criteria and the ECG episode pre-trigger durations. If changes are made to the arrhythmia trigger criteria, then changes may also be made to the ECG pre-trigger durations to ensure capture of the ECG onset and/or offset. In one embodiment, changes to the trigger criteria may be made automatically by medical device 200 during the monitoring process, or may be pushed to medical device 200 from an external source such as a HCP. In one embodiment, a change to the trigger criteria results in analysis and, if necessary, respective changes to the ECG pre- and post-trigger durations.

In this way, the onset trigger criteria is utilized to select an onset pre-trigger duration that ensures capture of the onset of the abnormal condition (e.g., arrhythmia), and an offset trigger criteria is utilized to select an offset pre-trigger duration that ensures capture of the offset of the abnormal condition. In some embodiments, the onset and offset of the detected abnormal condition may be the most clinically relevant. In these embodiments, it may be possible that a first ECG segment is captured with respect to the onset of the abnormal condition, followed by a pause, and then a second ECG segment is captured with respect to the detected offset of the abnormal condition. In this way, capture of onset and offset are ensured, but with a suspension or gap in recording between the captured onset and offset. If the portion of the abnormal condition between onset and offset is less clinically relevant, this provides efficient use of memory.

In addition, although FIG. 3 was described with respect to ECG monitoring to detect arrhythmic conditions, in other embodiments other types of physiological parameters may be monitored and utilized to detect abnormal conditions—both cardiac based and non-cardiac based.

FIG. 4 is a flowchart that illustrates selecting ECG episode pre- and post-trigger durations based on a plurality of arrhythmia trigger criteria and arrhythmia types according to an embodiment of the present invention. In the embodiment shown in FIG. 4, rather than calculate pre- and post-trigger durations for each arrhythmia trigger criteria, the embodiment shown in FIG. 4 calculates a pre- and post-trigger duration that will ensure capture of onset and/or offset for each arrhythmia trigger criteria.

At step 402, arrhythmia trigger criteria are selected and/or determined for a plurality of arrhythmia types. For example, arrhythmias may include tachycardia detection at a plurality of different beat rates (e.g., 130, 150, 165, and 180 BPM), as well as atrial fibrillation (AF). Each of the plurality of arrhythmia types may utilize different trigger criteria. For example, tachycardia trigger detection may require that 13 beats out of a total of 20 beats exceed a HR threshold (e.g., 130 BPM). In contrast, the AF trigger criteria may require that 40 beats out of a total of 45 beats exhibit an AF condition, and beats may exhibit AF characteristics at a much lower rate than tachycardia (e.g., as low as 60 BPM). The combination of these factors results in a greater amount of time being required to trigger detection of the AF condition than the tachycardia condition. In addition, in some embodiments the trigger criteria may be modified during operation for one or more of the arrhythmias, either automatically or in response to input received from a HCP. In addition, trigger criteria selected at step 402 may also include selection of offset trigger criteria for a plurality of arrhythmia types and may default to longer times for combination type arrhythmias.

At step 404, the plurality of selected/determined trigger criteria (which may also include offset trigger criteria) are analyzed to determine the appropriate trigger duration (time from onset to trigger or from offset to trigger) given the trigger criteria. In one embodiment, this determination is based on the maximum "Y" (X beats out of Y total beats) utilized by the plurality of trigger criteria. For example, if tachycardia trigger criteria utilizes 20 total beats in the trigger criteria and the AF trigger criteria utilizes 45 total beats in the trigger criteria, then the maximum "Y" value is 45 beats. In other embodiments, this determination is based in addition on the expected beats per minute of the arrhythmia being monitored. For example, while a tachycardia requires at least a certain number of beats to exceed a threshold heart rate (e.g., 130 BPM), AF may be detected in beats operating at much lower heart rates (e.g., 60 BPM). This information regarding possible heart rates of the various arrhythmias may also be accounted for in determining the appropriate onset duration to ensure capture of the onset for all arrhythmia types. Likewise, an appropriate offset trigger duration may be calculated based on the plurality of offset trigger criteria to ensure capture of the offset for all arrhythmia types.

At step 406, ECG episode pre-trigger durations are selected based on the likely maximum amount of time from onset or offset to satisfying the trigger criteria. For example, in the embodiment discussed above, AF trigger criteria utilized a higher Y value (e.g., 40 out of 45 total beats) than the tachycardia trigger criteria, and in addition may present itself at a lower heart rate than a tachycardia. As a result, ECG pre-trigger durations are selected to ensure that onset is captured with respect to AF trigger criteria. Similarly, offset pre-trigger durations are selected based on the maximum amount of time from offset to the offset trigger criteria to ensure that offset is captured for any of the plurality of offset trigger criteria.

In this way, the onset trigger criteria is utilized to select an onset pre-trigger duration that ensures capture of the onset of the abnormal condition (e.g., arrhythmia), and an offset trigger criteria is utilized to select an offset pre-trigger duration that ensures capture of the offset of the abnormal condition, despite the plurality of different types of abnormal conditions that may be detected. In some embodiments, the onset and offset of the detected abnormal condition may be the most clinically relevant. In these embodiments, it may be possible that a first ECG segment is captured with respect to the onset of the abnormal condition, followed by a pause, and then a second ECG segment is captured with respect to the detected offset of the abnormal condition. In this way, capture of onset and offset are ensured, but with a suspension or gap in recording between the captured onset and offset. If the portion of the abnormal condition between onset and offset is less clinically relevant, this provides efficient use of memory.

As discussed above, although FIG. 4 was described with respect to ECG monitoring to detect arrhythmic conditions, in other embodiments other types of physiological parameters may be monitored and utilized to detect abnormal conditions—both cardiac based and non-cardiac based. In addition, as discussed earlier, this may also include adding a buffer duration to the appropriate onset/offset trigger duration in order to add context to conditions just prior to onset and/or offset.

FIG. 5 is a flowchart that illustrates steps utilized to monitor ECG signals based on the appropriately selected pre- and post-trigger durations according to an embodiment of the present invention. For the sake of simplicity, the flowchart illustrated in FIG. 5 describes the capture of onset of an arrhythmia condition based on an appropriately selected pre-trigger duration. However, this example would apply in the same way to the capture of offset of an arrhythmia condition based on an appropriately selected post-trigger duration.

At step 502, ECG signal are monitored and are stored to buffer 212 while being analyzed by ECG analysis module 208. At step 504, a determination is made if the arrhythmia trigger criteria has been satisfied (i.e., triggered). For example, if the monitored ECG signal includes at least 20 beats out of 25 total beats that exceed the arrhythmia trigger criteria, then at step 504 the arrhythmia criteria is triggered and the ECG segment located in the buffer 212 is stored to memory 214 (or other appropriate storage location) at step 506. The pre-trigger duration (selected for example as described with respect to FIGS. 3 and 4) ensures that the captured ECG segment includes the onset of the arrhythmia. If the arrhythmia criteria triggered was related instead to the offset of the arrhythmia, then the post-trigger duration ensures that the captured ECG segment includes the offset of the arrhythmia. If at step 504 the arrhythmia trigger criteria is not triggered, then monitoring continues at step 502. In some embodiments, as ECG monitoring continues, ECG signals stored to the buffer 212 (shown in FIG. 2) are overwritten with more recent ECG signal, or if a circular buffer is not utilized then the contents of buffer 212 are discharged and new ECG signals are loaded into buffer 212. As discussed above, in one embodiment if an ECG segment is stored at step 506, this means that the ECG segment from the buffer is captured or written to a longer-term memory unit (e.g., memory 214).

At step 508, the ECG segment is analyzed to locate the onset beat within the stored ECG segment. In one embodiment, the analysis is performed locally by ECG analysis module included as part of medical device 200 (shown in FIG. 2). In other embodiments, the analysis is performed remotely on remote monitoring center 106 (shown in FIG. 1). Identification of the onset beat may be rate-based, morphologically-based, based on another criteria utilized to detect arrhythmias, or a combination thereof. For example, the first beat-to-beat threshold indicating a heart-rate above the tachycardia threshold may be identified as the onset beat within the stored ECG segment. In other embodiments, the first beat identified as including the morphology of a PVC beat is identified as the onset beat of the stored ECG segment. Similarly, step 508 may include analyzing an ECG segment to locate the offset beat within an ECG segment stored in response to a detected offset criteria being satisfied. Once again, a plurality of criteria may be utilized alone or in combination to detect the last beat representing an arrhythmic condition.

At step 510, a time between identified onset beat and the arrhythmic trigger criteria is measured. In one embodiment, the time between an identified onset beat and the arrhythmia trigger criteria being satisfied is an indication of how quickly the arrhythmia is organizing, which in turn is an indication of the severity of the arrhythmia. At step 512, the measured time is stored, and may be subsequently analyzed to determine severity of the arrhythmia, progress of the arrhythmia, as well as the efficacy of treatment. The same analysis may be utilized with respect to offset of arrhythmia, and may be utilized to monitor the severity of the detected arrhythmia, progress of the arrhythmia, as well as efficacy of treatment. In one embodiment, the measured times are stored in a histogram that allows a HCP to quickly compare the measured times over a period of time and make determination regarding the status of the arrhythmia.

FIG. 6 is a flowchart that illustrates utilization of an arrhythmia trigger criteria and an onset trigger criteria according to another embodiment of the present invention. In general, this embodiment relies on a higher sensitivity onset trigger to ensure capture of the onset of the arrhythmia, and the usual (i.e., standard, but relatively lower sensitivity) arrhythmia trigger criteria to capture the arrhythmia. For example, if during monitoring the higher sensitivity onset trigger criteria is satisfied, then a first ECG segment corresponding to the onset trigger criteria is captured (i.e., transferred from buffer 212 to memory 214, as shown in FIG. 2). Because the onset trigger criteria has a higher sensitivity, it will be triggered prior to the arrhythmia trigger criteria. Subsequently, if the arrhythmia trigger criteria is not triggered, then the ECG segment captured in response to the onset trigger criteria can be discarded. However, if the arrhythmia trigger criteria is triggered, then a second ECG segment is captured in response to the arrhythmia trigger criteria and the first ECG segment captured in response to the onset trigger criteria is retained. In this way, onset of an arrhythmia is captured by the higher sensitivity onset trigger criteria while the arrhythmia trigger is captured by a lower sensitivity trigger criteria. The same logic is applied to detecting arrhythmia offset condition as well. A benefit of this approach is that a smaller buffer may be utilized than otherwise required, because a separate ECG segment is captured for each of onset, arrhythmia trigger, and offset. In addition, some medical devices may not make use of a circular or rolling buffer such as that shown in FIG. 2. In these devices, ECG data may be stored to memory as a predetermined ECG segment. One drawback of this approach is that an arrhythmia that starts near the end of a first ECG segment may not be detected until the second ECG segment, at which point the first ECG segment has been discarded and onset of the arrhythmia lost. The embodiment shown in FIG. 5 cures this deficiency, as the onset trigger criteria is triggered in response to events within the first ECG segment, resulting in the first ECG segment being captured, while the onset trigger is verified during the second ECG segment. In this way, the embodiment shown in FIG. 5 may also be utilized to ensure capture of an arrhythmia onset despite utilization of a non-rolling buffer.

In particular, at step 602 arrhythmia trigger criteria and onset/offset trigger criteria are selected. Onset/offset trigger criteria are selected to provide a higher sensitivity than the arrhythmia trigger criteria. For example, the arrhythmia trigger criteria for a tachycardia (described above) may be triggered when 13 beats out of 20 total beats exceed a heart rate threshold. However, the onset trigger criteria may be triggered when 1 beat out of 2 total beats exceeds a heart rate threshold. In this way, the onset/offset trigger criteria is triggered much more easily than the arrhythmia trigger criteria (i.e. more sensitivity). The selected arrhythmia trigger criteria and onset trigger criteria may be selected based on information regarding the size of the buffer available, number of beats being utilized by the two trigger criteria, and expected heart rate associated with the underlying arrhythmias.

At step 604, ECG signals are monitored and are stored to buffer 212 while being analyzed by ECG analysis module 208. At step 606, a determination is made if the onset trigger criteria has been satisfied (i.e., triggered). For example, if the monitored ECG signal includes at least 1 beat out of 2 total beats that exceeds the onset trigger criteria, then at step 608 the onset criteria is triggered and the ECG segment located in the buffer 212 is stored to memory 214 (or other appropriate storage location). In this way, an ECG segment representing the potential onset of an arrhythmia is captured (referred to herein as an onset ECG). If at step 606 the arrhythmia onset criteria is not triggered, then monitoring continues at step 604. In some embodiments, as ECG monitoring continues, ECG signals stored to the buffer 212 (shown in FIG. 2) are overwritten with more recent ECG signal, or if a circular buffer is not utilized then the contents of buffer 212 are discharged and new ECG signals are loaded into buffer 212. As discussed above, if an onset ECG segment is stored at step 608, this means that the ECG segment from the buffer is captured or written to a longer-term memory unit (e.g., memory 214). However, capture of an onset ECG segment at step 608 does not mean that an arrhythmia has been triggered, only onset of a potential arrhythmia.

At step 610, monitoring of the ECG signal continues and a determination is made whether the arrhythmia criteria has been triggered. For example, in one embodiment, the arrhythmia criteria is triggered when 13 out of 20 total beats exceeds a heart rate threshold. If at step 610, the arrhythmia criteria is not triggered, this indicates that the arrhythmia onset that was triggered at 606 was a false alarm (i.e., not the onset of an actual arrhythmia). In response, at step 612 the stored ECG onset segment is discarded.

If at step 610 the arrhythmia criteria is satisfied (i.e. triggered), then at step 614 the ECG segment is captured and stored to the memory unit, and importantly, the stored ECG onset segment previously captured is not discarded. As a result, two separate ECG segments are captured, the first captured by the triggering of the arrhythmia onset criteria and the second ECG segment captured by the triggering of the arrhythmia trigger criteria. In other embodiments, capture of a first ECG segment and a second ECG segment may also be utilized to capture overlapping arrhythmias, each triggered in response to a different trigger criteria being satisfied.

A similar approach may be utilized to detect offset of an arrhythmia, with a higher sensitivity initial offset trigger criteria being utilized to trigger capture of a first ECG segment and a lower sensitivity offset trigger criteria being utilized to trigger capture of a second ECG segment. While the durations of the captured ECG segments may be shorter in this embodiment than in the embodiments discussed with respect to FIGS. 3 and 4, the ECG onset, trigger events, and offset are still captured, albeit via a plurality of separate ECG segments rather than one, long ECG segment. A benefit of this approach is that the size of buffer 210 (shown in FIG. 2) may be smaller than in embodiments in which the onset and trigger event (or alternatively offset and offset trigger event) must be captured by a single ECG segment while ensuring that onset and trigger (or offset and offset trigger) are captured. That is, the available memory space is utilized effectively while ensuring capture of the onset and offset of abnormal conditions such as arrhythmias. In particular, while the onset of an abnormal condition may be clinically relevant, along with a portion of the arrhythmia captured in response to the arrhythmia trigger criteria being satisfied, it may not be clinically relevant to store an entire arrhythmic condition. In one embodiment, there may be a gap in time between the first ECG segment captured in response to the onset trigger criteria and the second ECG segment captured in response to the arrhythmia trigger criteria. As discussed above, the embodiment shown in FIG. 6 is also beneficial in embodiments in which buffer 212 is not a rolling or circular buffer, and may even be relatively large in size. The embodiment shown in FIG. 6 ensures that onset of an arrhythmia occurring in a first ECG segment is captured via utilization of the higher sensitivity onset trigger, even though the arrhythmia trigger does not occur until the subsequent ECG segment.

In the embodiment shown in FIG. 6, the first ECG segment is discarded if the arrhythmia trigger criteria is not satisfied. In one embodiment, however, even if the first ECG segment is discarded a count or tally is maintained of the number of onset (or offset) trigger criteria satisfied. For example, the onset trigger criteria may be satisfied a number of times before the arrhythmia trigger criteria is satisfied. While the ECG segments captured in response to the onset trigger criteria being satisfied may be discarded if the arrhythmia trigger criteria is not satisfied, the number of times the onset trigger criteria is satisfied may be clinically relevant. Therefore, additional information may be stored with respect to the triggering of the onset trigger criteria, even if no ECG segment is stored. This may include a count of the number of times the onset trigger criteria is satisfied, histogram of the time/duration of onset triggers as a measure of rhythm organization and disease severity, as well as other metrics.

Figure 7:
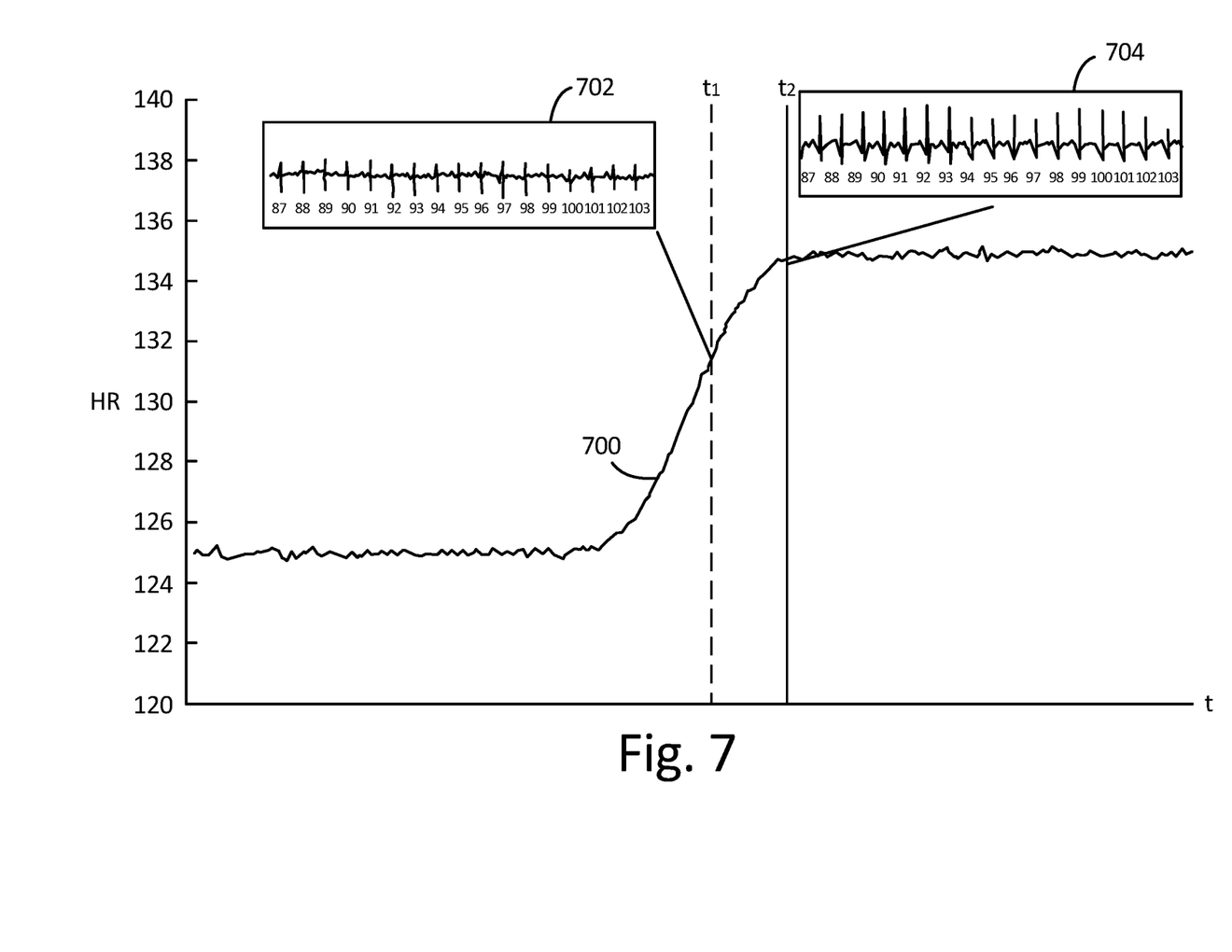
FIG. 7 is a graph that illustrates timing associated with onset criteria triggering and arrhythmia criteria triggering according to an embodiment of the present invention.

FIG. 7 is a graph that illustrates timing associated with onset criteria triggering and arrhythmia criteria triggering according to an embodiment of the present invention. In the embodiment shown in FIG. 7, the heart rate (y-axis) of a patient monitored over time t (x-axis) is illustrated by line 700. Monitoring of the ECG signal continues along time t, with the monitored ECG signal being continuously analyzed to detect whether the onset trigger criteria has been satisfied (step 606 in FIG. 6), and if so, whether the arrhythmia onset criteria has been satisfied (step 610 in FIG. 6). In the example illustrated in FIG. 7, at time $t_1$ the onset trigger criteria is satisfied, resulting in the capture of the ECG onset segment 702. Assuming the pre- and post-trigger durations were properly selected based on the arrhythmia being monitored, then ECG onset segment 702 captures the portion of the ECG signal representing onset of the arrhythmia, which occurs at some point in time prior to time $t_1$. Monitoring continues, and in the embodiment shown in FIG. 7 at time $t_2$ the arrhythmia trigger criteria is satisfied, resulting the capture of a second ECG segment 704. In particular, because the onset trigger criteria is defined to be more sensitive than the arrhythmia trigger criteria, the onset trigger criteria will always be satisfied before the arrhythmia trigger criteria.

Figure 8:
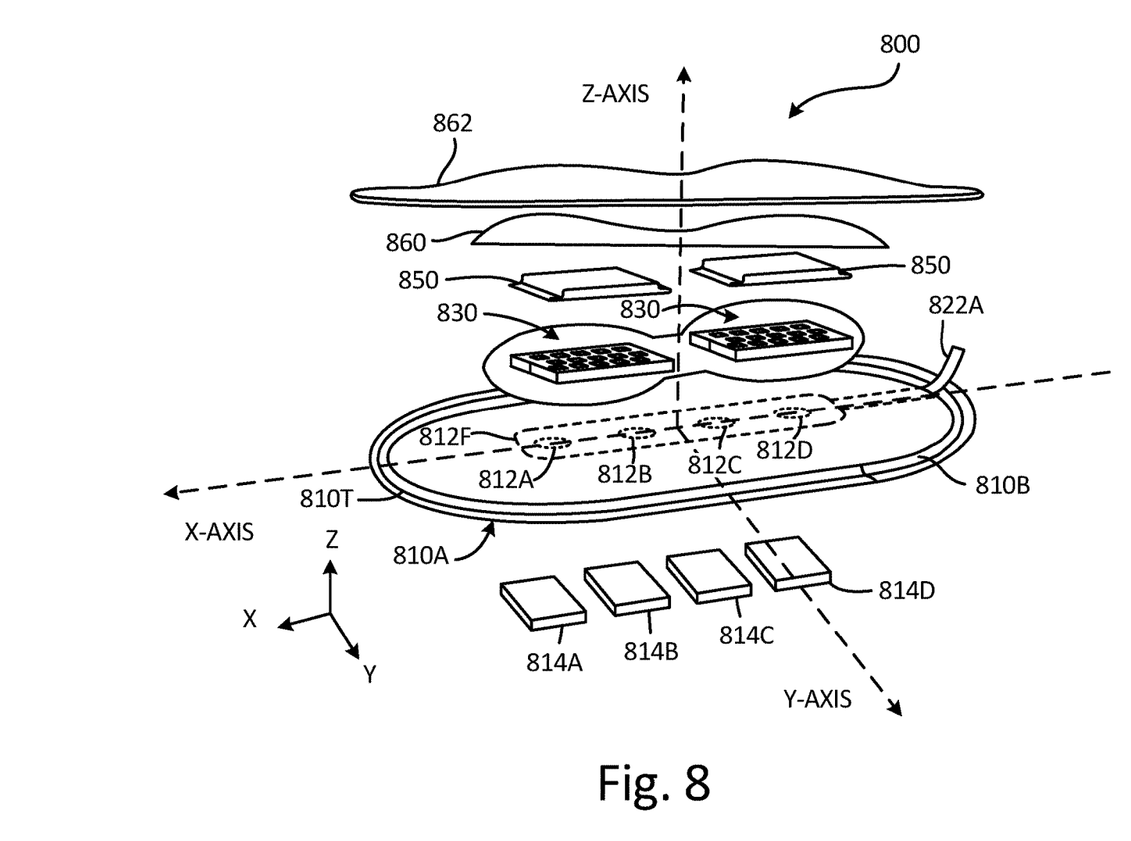
FIG. 8 is an exploded view of a medical device utilized to monitor and analyze one or more physiological parameters according to an embodiment of the present invention.

FIG. 8 is an exploded view, respectively, of medical device 800 that may be utilized according to one or more embodiments of the present disclosure. In the embodiment shown in FIG. 8, medical device 800 is an adherent device, but as described above may also be implemented as an implantable device, an injectable device, or similar wearable device. In the embodiment shown in FIG. 8, adherent device 800 includes adherent tape 810T, electrodes 812A, 812B, 812C, 812D with gels 814A, 814B, 814C, 814D, printed circuit board (PCB) 820, flexible connected 822A, electrical components/sensors 830 mounted on PCB 820, batteries 850, electronics housing cover 860, and flexible cover 862.

Adherent device 800 comprises at least two electrodes—although the embodiment shown in FIG. 8 includes electrodes 812A, 812B, 812C and 812D. The adherent patch 800 comprises a first side, or a lower side 810A, that is oriented toward the skin of the patient when placed on the patient. The adherent patch 800 may also comprise a tape 810T which is a material, preferably breathable, with an adhesive (not shown) to adhere to patient P. Electrodes 812A, 812B, 812C and 812D are affixed to adherent patch 800. In many embodiments, at least four electrodes are attached to the patch. Gels 814A, 814B, 814C and 814D can each be positioned over electrodes 812A, 812B, 812C and 812D, respectively, to provide electrical conductivity between the electrodes and the skin of the patient. Adherent patch 800 also comprises a second side, or upper side 810B. In many embodiments, electrodes 812A, 812B, 812C and 812D extend from lower side 810A through adherent patch 100 to upper side 810B. An adhesive can be applied to upper side 810B to adhere structures, for example a breathable cover, to the patch such that the patch can support the electronics and other structures when the patch is adhered to the patient. In many embodiments, adherent patch 100 may comprise a layer of breathable tape 810T, for example a tricot-knit polyester fabric, to allow moisture vapor and air to circulate to and from the skin of the patient through the tape. Electrical signals received at electrodes 812A-812D may be communicated to electronic components 830 via flexible connection 822A, which is connected to a PCB (not shown). Cover 860 is positioned over batteries 850 and electronic components 830 to provide protection for both. In addition, flexible cover 862 is positioned to encase the flexible PCB 820, electronics components 830, and/or adherent patch 810 so as to protect at least the electronics components and the PCB In addition, electronic components 830 may include ECG circuitry utilized to generate electrocardiogram signals and data from two or more of electrodes 812A, 812B, 812C and 812D in many ways. In some embodiments, ECG circuitry (not shown) is connected to inner electrodes 812B and 812C, which may comprise sense electrodes of the impedance circuitry as described above. In many embodiments, the ECG circuitry may measure the ECG signal from electrodes 812A and 812D when current is not passed through electrodes 812A and 812D. In addition, electronic components 830 may include bioimpedance circuitry connected to two or more of electrodes 812A, 812B, 812C and 812D to allows electronic components 830 to measure a bioimpedance associated with the patient. In addition, electronic components 830 may include an accelerometer configured to measured motion of the patient.

In addition, electronic circuitry 830 may comprise a processor module that can be configured to analyze physiological parameters monitored by adherent device 800 and to control collection and transmission of data from the electrocardiogram circuitry. In one embodiment, the processor module included as part of electronic circuitry 830 comprises a tangible medium, for example read only memory (ROM), electrically erasable programmable read only memory (EEPROM) and/or random access memory (RAM). Tangible medium may, for example, to implement one or more circular buffers 212 (shown in FIG. 2) and/or memory 214 (also shown in FIG. 2). Processing of monitored physiological parameters such as ECG signals may be distributed between the local processor module included as part of electronic circuitry 830 and remote monitoring system 106 (shown in FIG. 1). In addition, the processor module may be capable of implementing one or more of the methods described with respect to FIGS. 3-5 to ensure capture of onset and/or offset conditions associated with an abnormal condition.

In one embodiment, a processor and/or a processing module include electronic circuitry configured to process monitored physiological signals of a patient using the trigger criteria selected and pre- and post-trigger durations selected in response to the trigger criteria, and capture clinically relevant segments that ensure capture of onset and/or offset of abnormal conditions. The processor and/or processing module may also communicate and/or transmit monitored physiological parameters and/or captured segments to a remote monitoring center for review by a HCP.

In many embodiments, electronics components 830 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the ECG signal or other physiological parameters collected by the adherent device 800. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection. For example, in one embodiment a HCP may push updated trigger criteria to the adherent device 800. In response, the processing module may select modified pre- and post-trigger durations.

Figure 9:
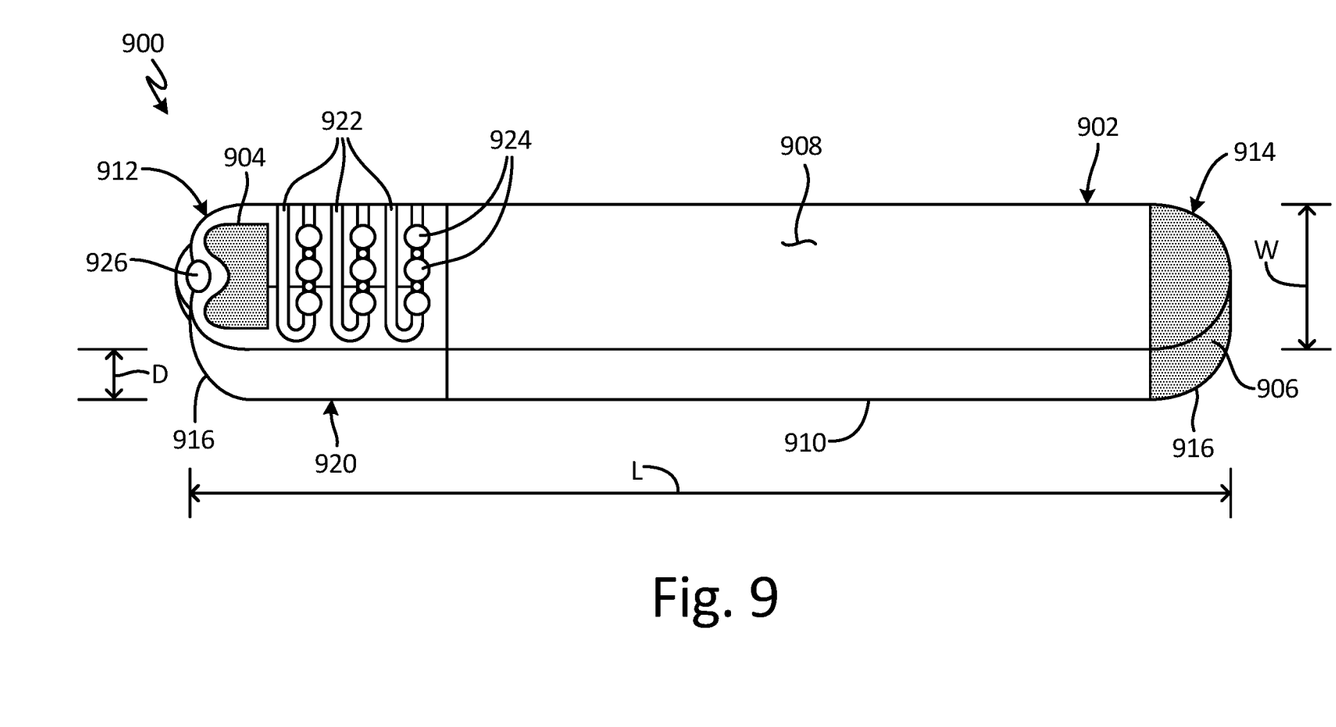
FIG. 9 is a perspective view of an insertable monitoring device according to an embodiment of the present invention.

FIG. 9 is a perspective view of an insertable medical device 900 according to an embodiment of the present invention. In the embodiment shown in FIG. 9, medical device 900 is an insertable cardiac monitor defined by a length L, a width W and thickness or depth D and is in the form of an elongated rectangular prism wherein the length L is much larger than the width W, which in turn is larger than the depth D. In one embodiment, the geometry of the insertable cardiac monitor 900—in particular a width W greater than the depth D—is selected to allow the cardiac monitor 900 to be inserted under the skin of the patient using a minimally invasive procedure and to remain in the desired orientation during insert.

In the embodiment shown in FIG. 9, once inserted within the patient, the first major surface 908 faces outward, toward the skin of the patient while the second major surface 910 is located opposite the first major surface 908. In addition, in the embodiment shown in FIG. 9, proximal end 912 and distal end 914 are rounded to reduce discomfort and irritation to surrounding tissue once inserted under the skin of the patient.

As described with other embodiments, proximal electrode 904 and distal electrode 906 are used to sense cardiac signals for determining abnormal cardiac events (e.g., bradycardia, tachycardia, etc.). A buffer (not shown) is included within insertable cardiac, along with memory utilized to store captured ECG segments. Captured ECG segments may be transmitted via integrated antenna 922 to another medical device, which may be another implantable device or an external device, or to a remote monitoring center. In alternative applications, electrodes 904 and 906 may be used for sensing any bio-potential signal of interest, which may be, for example, an EGM, EEG, EMG, or a nerve signal, from any implanted location.

In the embodiment shown in FIG. 9, proximal electrode 904 is in close proximity to the proximal end 912 and distal electrode 906 is in close proximity to distal end 914. In this embodiment, distal electrode 906 is not limited to a flattened, outward facing surface, but may extend from first major surface 908 around rounded edges 916 and onto the second major surface 910 so that the electrode 906 has a three-dimensional curved configuration. In the embodiment shown in FIG. 9, proximal electrode 904 is located on first major surface 908 and is substantially flat, outward facing. However, in other embodiments proximal electrode 904 may utilize the three dimensional curved configuration of distal electrode 906, providing a three dimensional proximal electrode (not shown in this embodiment). Similarly, in other embodiments distal electrode 906 may utilize a substantially flat, outward facing electrode located on first major surface 908 similar to that shown with respect to proximal electrode 904. The various electrode configurations allow for configurations in which proximal electrode 904 and distal electrode 906 are located on both first major surface 908 and second major surface 910. In other configurations, such as that shown in FIG. 9, only one of proximal electrode 904 and distal electrode 906 is located on both major surfaces 908 and 910, and in still other configurations both proximal electrode 904 and distal electrode 906 are located on one of the first major surface 908 or the second major surface 910 (i.e., proximal electrode 904 located on first major surface 908 while distal electrode 906 is located on second major surface 910). In another embodiment, insertable monitoring device 900 may include electrodes on both major surface 908 and 910 at or near the proximal and distal ends of the device, such that a total of four electrodes are included on insertable monitoring device 900. Electrodes 904 and 906 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 9, proximal end 912 includes a header assembly 920 that includes one or more of proximal electrode 904, integrated antenna 922, anti-migration projections 924, and/or suture hole 926. Integrated antenna 922 is located on the same major surface (i.e., first major surface 908) as proximal electrode 904 and is also included as part of header assembly 920. Integrated antenna 922 allows insertable monitoring device 900 to transmit and/or receive data. In other embodiments, integrated antenna 922 may be formed on the opposite major surface as proximal electrode 904, or may be incorporated within the housing 922 of insertable monitoring device 900. In one embodiment, electronic circuitry (not shown) may be housed within housing 922. As described above with respect to FIG. 9, electronic circuitry may include a tangible medium for storing the trigger criteria along with the selected pre- and post-trigger durations to be utilized to ensure capture of onset and/or offset conditions. In addition, electronic circuitry may include sensing circuitry for sensing one or more physiological parameters, such as ECG signals, accelerometer signals, and/or bio-impedance signals, and may include a processor module for processing monitored ECG signals to detect arrhythmic ECG segments based on the heart-rate thresholds and rate-based sensitivity levels.

In the embodiment shown in FIG. 9, anti-migration projections 924 are located adjacent to integrated antenna 922 and protrude away from first major surface 908 to prevent longitudinal movement of the device. In the embodiment shown in FIG. 9, anti-migration projections 924 includes a plurality (e.g., nine) small bumps or protrusions extending away from first major surface 908. As discussed above, in other embodiments anti-migration projections 924 may be located on the opposite major surface as proximal electrode 904 and/or integrated antenna 922. In addition, in the embodiment shown in FIG. 9 header assembly 920 includes suture hole 926, which provides another means of securing insertable monitoring device 900 to the patient to prevent movement following insert. In the embodiment shown, suture hole 926 is located adjacent to proximal electrode 904. In one embodiment, header assembly 920 is a molded header assembly made from a polymeric or plastic material, which may be integrated or separable from the main portion of insertable monitoring device 900.

In this way, the present invention provides systems and methods of monitoring physiological parameters and capturing abnormal segments, wherein captured segments include onset and/or offset conditions associated with the detected abnormal condition. In one embodiment, pre-trigger durations are selected based on the trigger criteria and/or offset trigger criteria being utilized to ensure that the triggering and capture of a segment in response to a triggering event includes the onset and/or offset of the detected abnormal condition. In other embodiments, this may include reviewing the plurality of different types of abnormal conditions being detected (e.g., different types of arrhythmias, etc.), and the plurality of different trigger criteria being utilized to select pre-trigger durations that ensure for each of the different types of abnormal conditions and trigger criteria that the onset and/or offset conditions are captured. In yet another embodiment, rather than increase the pre-trigger durations to ensure capture of onset and/or offset conditions, a secondary onset (as well as offset) trigger criteria may be utilized to trigger capture of the onset of an abnormal condition, wherein the captured onset segment is discarded if no subsequent abnormal condition (e.g., arrhythmia) is triggered. In this way, the present invention ensures that captured segments include onset and/or offset conditions associated with a triggered condition. Having captured onset and/or offset, parameters such as length of time from onset to trigger criteria being satisfied may be determined and utilized to monitor the severity, progression, and/or efficacy of treatment.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A medical device for monitoring physiological parameters of a patient and capturing segments of the monitored physiological parameters, the medical device comprising: circuitry configured to monitor a one or more physiological parameters associated with the patient; and an analysis module that includes a buffer to store monitored physiological parameters and a processor to analyze monitored physiological parameters and trigger capture of segments from the buffer in response to a triggering criteria being satisfied, wherein a size of the segment captured in response to a triggering event depends at least in part on a pre-trigger duration, wherein the analysis module selects the pre-trigger duration based at least in part on the triggering criteria.

2. The medical device claim 1, wherein the circuitry is electrocardiogram (ECG) circuitry coupled to one or more electrodes to monitor an ECG signal associated with the patient.

3. The medical device of claim 2, wherein the triggering criteria defines a number of beats (X) that must exceed a heart rate threshold out of a total number of beats (Y), wherein the pre-trigger duration is selected based at least in part on the total number of beats (Y).

4. The medical device of claim 3, wherein the pre-trigger duration is selected based at least in part on a type of arrhythmia being detected by the triggering criteria.

5. The medical device of claim 3, wherein the triggering criteria includes a plurality of triggering criteria, each triggering criteria associated with one of a plurality of types of arrhythmia, and wherein the pre-trigger duration is selected based on a maximum trigger duration associated with the plurality of triggering criteria.

6. The medical device of claim 5, wherein the pre-trigger duration is selected based on the maximum total number of beats (Y) value utilized by the plurality of triggering criteria.

7. The medical device of claim 1, wherein the triggering criteria includes an onset triggering criteria and an offset triggering criteria, wherein the pre-trigger duration is selected based on the onset triggering criteria and an offset pre-trigger duration is selected at least in part based on the offset triggering criteria.

8. The medical device of claim 1, wherein the processor identifies onset of condition resulting in triggering criteria being satisfied and measures a time from onset to the triggering criteria.

9. The medical device of claim 8, wherein the measured time from onset to the triggering criteria is stored and subsequently analyzed to determine one or more of severity of the condition, progression of the condition, and efficacy of treatment.

* * * * *